United States Patent
Ho et al.

(10) Patent No.: US 6,627,623 B2
(45) Date of Patent: Sep. 30, 2003

(54) INDUCING CELL APOPTOSIS AND TREATING CANCER USING 1-O-ACETYLBRITANNILACTONE OR 1,6-O,O-DIACETYLBRITANNILACTONE

(75) Inventors: Chi-Tang Ho, East Brunswick, NJ (US); Mohammed Rafi, Highland Park, NJ (US); Robert S. Dipaola, Long Valley, NJ (US); Geetha Ghai, Murray Hill, NJ (US); Robert T. Rosen, Cranbury, NJ (US); Naisheng Bai, Piscataway, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 10/079,038

(22) Filed: Feb. 20, 2002

(65) Prior Publication Data

US 2002/0155178 A1 Oct. 24, 2002

Related U.S. Application Data

(60) Provisional application No. 60/270,189, filed on Feb. 21, 2001.

(51) Int. Cl.[7] ...................... A61K 35/78; A61K 31/585; A01N 65/00; C12N 5/00; C12N 5/02
(52) U.S. Cl. ........................ 514/175; 424/725; 424/764; 424/778; 435/325
(58) Field of Search ................................ 424/725, 764, 424/778; 435/410, 418, 416, FOR 114, FOR 100, 52, 124; 514/783, 175

(56) References Cited

U.S. PATENT DOCUMENTS 5,853,727 A * 12/1998 Cohen
6,051,565 A * 4/2000 Shaikenov et al.
6,080,741 A * 6/2000 Adekenov

FOREIGN PATENT DOCUMENTS

JP          9-249578      *  9/1987
WO          WO43314       *  9/1999

OTHER PUBLICATIONS

Zhou et al., Sesquiterpene Lactones from Inual Britannica, Phytochemistry, 1993, vol. 34, No. 1, pp. 249–252.

Park et al., Cytotoxic Sesquiterpene Lactones From Inula Britannica, Planta Medica, 1998, vol. 64, No. 8, pp. 752–754.

* cited by examiner

*Primary Examiner*—David M. Naff
*Assistant Examiner*—Deborah K. Ware
(74) *Attorney, Agent, or Firm*—Reed Smith LLP; William J. McNichol, Jr.; Nanda P. B. A. Kumar

(57) ABSTRACT

Compositions and methods for preventing and treating cancer are provided that comprise extracts of *Inula britannica* or compounds isolated therefrom. The compounds of 1-O-acetylbritannilactone or 1,6-O,O-diacetylbritannilactone are isolated and used for inducing apoptosis in cells and for treating cancer in an animal. Induction of apoptosis comprises contacting cells with a composition comprising the compounds in an amount sufficient to induce Bcl-2 protein phosphorylation. Further, treatment of cancer in an animal comprises administering to an animal a composition comprising the compounds in an amount sufficient to induce Bcl-2 protein phosphorylation to treat the cancer.

6 Claims, No Drawings

INDUCING CELL APOPTOSIS AND TREATING CANCER USING 1-O-ACETYLBRITANNILACTONE OR 1,6-O,O-DIACETYLBRITANNILACTONE

INTRODUCTION

This application claims the benefit of priority from U.S. provisional application Ser. No. 60/270,189, filed Feb. 21, 2001.

BACKGROUND OF THE INVENTION

*Inula britannica* is a traditional Chinese medicinal herb that has been used to treat bronchitis and inflammation. A variety of this plant, known as *Inula britannica chinensis* has been used as an insecticide in certain areas of China. Both *Inula britannica* and *Inula britannica chinensis* have been examined in order to determine the chemical constituents responsible for its pharmacological effects. A variety of sesquiterpenes have been isolated. In the case of *Inula britannica chinensis*, three specific sesquiterpene lactones were identified, including britannilactone, 1-O-acetylbritannilactone, and 1,6-O,O-diacetylbritannilactone (Zhou, B-N. et al. 1993. *Phytochemistry* 34:249–252).

Some natural plant extracts have been shown to have activity as chemopreventive agents. An example, taxol, acts by inducing Bcl-2 phosphorylation in cancer cells which leads to programmed cell death (Haldar, S. Et al. 1996. *Cancer Res.* 56:1253–1255). The Bcl-2 protein is a member of a family of cytoplasmic proteins which regulates cell death. Bcl-2 has been shown to promote cell survival by inhibiting the process of cell death known as apoptosis. Whereas Bcl-2 acts to inhibit apoptosis, Bax, another cytoplasmic protein, counteracts this protective effect; Bcl-2 is also thought to protect cells from apoptosis by dimerizing with Bax (Hunter, J. J. et al. 1996. *J. Biol. Chem.* 271:8521–8524). The phosphorylation of Bcl-2 interferes with the homodimers and subsequent apoptosis (Haldar, S. et al. 1995. *Proc. Natl. Acad. Sci. USA* 92:4507–4511; Haldar, S. Et al. 1996. *Cancer Res.* 56:1253–1255). Therefore, therapeutic strategies to inactivate Bcl-2 are being sought as a way to improve clinical results with certain drugs. It has now been found that an extract of *Inula britannica* has activity relevant to prevention and treatment of cancer due to its activity to phosphorylate Bcl-2.

SUMMARY OF THE INVENTION

An object of the present invention is a composition that induces apoptosis in cells which comprises an extract of *Inula Britannica* or compounds isolated therefrom. In a preferred embodiment the composition comprises sesquiterpene lactone.

Another object of the present invention is a method for inducing apoptosis in cells comprising contacting cells with an extract of *Inula Britannica* or compounds isolated therefrom so that apoptosis is induced.

Yet another object of the present invention is a method for preventing and treating cancer which comprises administering an effective amount of extract of *Inula Britannica* or compounds isolated therefrom.

DETAILED DESCRIPTION OF THE INVENTION

An extract of *Inula britannica* has been isolated that has use as a cancer preventative agent due to its activity to induce apoptosis in cancer cells. The extract contains several sesquiterpene compounds, including but not limited to the sesquiterpene lactones known as britannilactone, 1-O-acetylbritannilactone (OABL), and 1,6-O,O-diacetylbritannilactone (OODABL). The extract and the chemicals isolated therefrom can be used as a pharmaceutical for cancer treatment and/or prevention as well as a medical food, or nutraceutical, and a dietary supplement.

The flowers (approximately 10 kg) of *Inula britannica* var. *chinensis* were extracted three times with 95% ethanol. The chloroform-soluble fraction of the ethanol extract (500 g) was chromatographed on a silica gel column eluting with a gradient of chloroform-methanol. From the fraction collected with chloroform-methanol (20:1), 1,6-O,O-diacetylbritannilactone (52 g) was obtained. From the fraction collected with chloroform-methanol (10:1), 1-O-acetylbritannilactone (10.5 g) was obtained.

Experiments were performed to determine the activity of two of the sesquiterpene compounds isolated from *Inula britannica*, OABL and OODABL, as cancer preventative agents. Using a Western blot technique, the ability of these compounds to phosphorylate Bcl-2 in cancer cells was examined. Using the breast cancer cell line MCF-7, it was found that OABL induced Bcl-2 phosphorylation, with effective doses of 10 and 20 $\mu$M. OODABL induced Bcl-2 phosphorylation at lower effective doses, 2.5 and 5 $\mu$M. These results were compared to the ability of a known chemotherapeutic paclitaxel, which induced Bcl-2 phosphorylation at a dose of 100 $\mu$M. These data indicate that the sesquiterpenes are more potent than paclitaxel at inducing Bcl-2 phosphorylation in MCF-7 cells.

In two ovarian cancer cell lines, OVCAR and PA-1, similar results were seen. In OVCAR cells, OODABL induced Bcl-2 phosphorylation at a dose of 5 $\mu$M, while OABL induced Bcl-2 phosphorylation at a dose of 10 $\mu$M. In PA-1 cells, OODABL induced Bcl-2 phosphorylation at a dose of 5 $\mu$M, while OABL induced Bcl-2 phosphorylation at a dose of 10 $\mu$M.

In a prostate cancer cell line, these compounds were also able to induce Bcl-2 phosphorylation. OODABL induced Bcl-2 phosphorylation at a dose of 5 $\mu$M while OABL induced Bcl-2 phosphorylation at a dose of 10 $\mu$M.

Using cleavage of PARP as an indicator of apoptosis, the compositions of the present invention were tested in PA-1 ovary cells. PARP is a 116 kD nuclear poly (ADP-ribose) polymerase that appears to be involved in DNA-repair, predominantly in response to environmental stress (Satoh, M. S. and T. Lindahl. 1992. *Nature* 356:356–358). PARP is important for cells to maintain their viability. Cleavage of PARP facilitates cellular disassembly and serves as a marker of cells undergoing apoptosis (Oliver, F. J. et al. 1998. *J. Biol. Chem.* 273:33533–33539). This protein can be cleaved by many ICE caspases to form a 85 kD protein in cells undergoing apoptosis. PA-1 cells were treated with OODABL for 24 hours. Cells were lysed and PARP cleavage was measured by Western Blot using a monoclonal antibody to PARP (Pharmingen, Inc., San Diego, Calif.). OABL induced PARP cleavage at doses of 10 and 20 $\mu$M, while OODABL induced PARP cleavage at a dose of 5 $\mu$M.

The effect of OODABL on cell cycle was analyzed by flow cytometery using breast cancer cell lin T47D. OODABL arrested cells at the G2/M phase at a 20 $\mu$M concentration as compared to control cells.

The effect of OODABL on microtubules was examined by indirect immunofluorescence of MCF-7 cells using an antibody to tubulin after 12 hours treatment with either a vehicle control, 10 $\mu$M paclitaxel (positive control), or 20 $\mu$M OODABL. The results showed, that OODABL polymerized microtubules like paclitaxel.

In a TUNEL assay, the effect of OODABL on late apoptosis was examined. HL-60 cells lines were subjected to flow cytometry analysis using APO-BRDU. Apoptosis was detected by incorporation of Br-dUTP using a fluorescein labeled anti-BrdU monoclonal antibody after treatment with a vehicle control, 1 $\mu$M camptothecin or 20 $\mu$M OODABL for 12 hours. OODABL was shown to induce apoptosis, as did the positive control camptothecin.

Cell viability was then assessed in a microculture tetrazolium/formazan assay (MTT; Scudiero, D. A. et al. 1988. *Cancer Res.* 48:4827–4833) using a variety of cell lines. Absorbance was measured at 550 nm and cell viability was expressed as the percentage of drug treated cells relative to that of controls. The $IC_{50}$ was then defined as the concentration of drug that produced a 50% decrease in cell viability relative to controls. OODABL was first tested in a variety of cell lines. Results in MCF-7 cells treated with various concentrations of OODABL (1.25, 12.5, 25. 50 and 100 $\mu$M OODABL) showed that cell viability decreased with treatment in a dose-dependent manner. The $IC_{50}$ was less than 12.5 $\mu$M. In PA-1 cells treated with various concentrations of OODABL (1.953, 3.9, 7.815, 15.625, 31.25, and 62.5 $\mu$M OODABL), cell viability was decreased in a dose-dependent manner with an $IC_{50}$ of less than 7.815 $\mu$M. In DU-145 cells treated with various concentrations of OODABL (3.4, 7.86, 15.6, 31.5, 62.5, and 125 $\mu$M OODABL), cell viability was decreased in a dose-dependent manner with an $IC_{50}$ of less than 15.6 $\mu$M. In NCI-H-460 cell treated with various concentrations of OODABL (3.9, 7.81, 1`5.62, 31.25, 62.5 and 125 $\mu$M OODABL), cell viability was decreased in a dose-dependent manner with an $IC_{50}$ of between 31.25 and 62.5 $\mu$M. In NIH 3T3 (normal mouse fibroblasts) cells treated with various concentrations of OODABL (1, 10, 20 and 50 $\mu$M OODABL), cell viability was decreased in a dose-dependent manner with an $IC_{50}$ of 50 $\mu$M.

OABL was then tested in some of these same cell lines. In MCF-7 cells, OABL was tested at doses of 0.3 nm, 3 nm, 30 nm, 300 nm, 3 $\mu$M, and 30 $\mu$M. Results showed that OABL decreased cell viability with an $IC_{50}$ of around 200 $\mu$M. In PA-1 cells, OABL (1.953, 3.9, 7.815, 15.62, 31.25 and 62.5 $\mu$M) decreased cell viability with an $IC_{50}$ of about 2 $\mu$M. In Du-145 cells, OABL (4.68, 9.37, 18.75, 37.5, 75 and 100 $\mu$M) decreased cell viability.

Cell cytotoxicity was also assessed by a clonogenic assay. MCF-7 breast cells were treated with various concentrations of OODABL (625 nm, 1.25, 2.5, 5 and 10 $\mu$M) for 15 days and cells were then stained with methylene blue and colonies counted. The $IC_{50}$ was in the range of 2.5 to 5 $\mu$M OODABL. PC-3 prostate cells were treated with various concentrations of OODABL (20 and 200 nm, and 2 and 20 $\mu$M) for 15 days and cells were then stained with methylene blue and colonies counted. The $IC_{50}$ was in the range of 200 nm OODABL. RKO cells were treated with various concentrations of OODABL (20 and 200 nm, and 2 and 20 $\mu$M) for 15 days and cells were then stained with methylene blue and colonies counted. The $IC_{50}$ was in the range of 20 $\mu$M OODABL. Baby rat kidney cells were transformed with E1A and transfected with the Bcl-2 gene to form BRK-4B-Bcl-2 cells. These cells were treated with various concentrations of OODABL (20 and 200 nm, and 2, 10 and 20 $\mu$M) for 15 days and cells were then stained with methylene blue and colonies counted. The $IC_{50}$ was in the range of 200 nM OODABL. Baby rat kidney cells were transformed with E1A and transfected with Bcl-2 gene in which phosphorylation sites were mutated to form phosphomutant BRK-4B-Bcl-2 cells. These cells were treated with various concentrations of OODABL (20 and 200 nm, and 2 and 20 $\mu$M) for 15 days and cells were then stained with methylene blue and colonies counted. The $IC_{50}$ was in the range of 2 $\mu$M.

The level of Bcl-2 phosphorylation was then assessed in the non-mutated and mutated BRK-4B-Bcl-2 cells using a Western blot assay. Cells were initially treated for 12 hours with the test compound, OODABL (at concentrations of 10, 20, 30, 40, or 60 $\mu$M). Taxol was used as a positive control at a concentration of 5 $\mu$M. Cells were then lysed in ice cold radio-immune precipitation buffer with inhibitors. Equivalent amounts of proteins were electrophoresed by 12% dodecyl sulfate-polyacrylamide gel electrophoresis and transferred to nitrocellulose. Bcl-2 and phosphorylated Bcl-2 proteins were detected using a monoclonal Bcl-2 primary antibody and a secondary goat anti-mouse horseradish peroxidase conjugated antibody followed by enhanced chemiluminescence detection. The results showed that there was a dose-dependent increase in Bcl-2 phosphorylation with OODABL in the non-mutated cells. Taxol also produced an increased in protein phosphorylation. In the mutated rat kidney cells, there was no phosphorylation evident with either taxol or OODABL.

These data demonstrate that the extract of *Inula britannica* has use as a cancer preventative and treatment agent due to its activity to induce apoptosis and cell cytotoxicity in cancer cells. The extract and the chemicals isolated therefrom, OABL and OODABL, can be used as a pharmaceutical for cancer treatment and/or prevention as well as a medical food, or nutraceutical, and a dietary supplement.

The data presented support the development of either foods for animal consumption, where animals include humans, or as dietary supplements for animals including humans. These foods and supplements are referred to by those of skill in the art as "nutraceuticals". Compositions of the present invention would be useful as nutraceuticals for prevention or treatment of cancer. One of skill would be able to use the results of experiments in cells and animals to determine an effective amount to be administered in humans. An effective amount would be an amount that induces apoptosis or inhibits tumor growth either in vitro or in vivo in animals. For example, human test doses can be extrapolated from effective doses in cell studies, such as $IC_{50}$ values, or from effective doses in vivo by extrapolating on a body weight or surface area basis. Such extrapolations are routine in the art. Further, one of skill would know how to formulate or prepare diets or dietary supplements containing the analogs. In the case of animal diets, the analogs could be added in concentrations up to 5% by weight and mixed according to methods routine in the art.

Dietary supplements for animals or humans could be prepared in a variety of forms that would include but not be limited to liquid, powder, or solid pill forms. Pill forms for the supplements would be prepared by methods routine in the art of dosage formulation and could include but not be limited to production of gel capsules, time-release capsules, or solid pills formulated with excipients and binders. Again, one of skill in the art would know how to formulate the extracts or compounds isolated therefrom based on its chemical nature and the desired effect. The extract and/or the compounds isolated therefrom could also be administered topically in liquid or creme of lotion forms or by injection. Injectable forms would be prepared by solubilizing in a pharmaceutically acceptable vehicle.

What is claimed is:

1. A method for inducing apoptosis in animal cells by inducing Bcl-2 protein phosphorylation in said cells comprising contacting said cells with a composition consisting essentially of 1-O-acetylbritannilactone or 1,6-O,O-diacetylbritannilactone in an amount sufficient to induce said phosphorylation to induce said apoptosis.

2. The method of claim 1, wherein the composition consists essentially of 1-O-acetylbritannilactone.

3. The method of claim 1, wherein the composition consists essentially of 1,6-O,O-diacetylbritannilactone.

4. A method for treating cancer by inducing Bcl-2 protein phosphorylation in an animal comprising administering to an animal a composition consisting essentially of 1-O-acetylbritannilactone or 1,6-O,O-diacetylbritannilactone in an amount sufficient to induce said phosphorylation to treat said cancer.

5. The method of claim 4, wherein the composition consists essentially of 1-O-acetylbritannilactone.

6. The method of claim 4, wherein the composition consists essentially of 1,6-O,O-diacetylbritannilactone.

* * * * *